United States Patent [19]

Miyake et al.

[11] Patent Number: 5,079,959
[45] Date of Patent: Jan. 14, 1992

[54] ANALYZING SYSTEM USING SHEATH FLOW OF SAMPLE

[75] Inventors: Ryo Miyake, Ibaraki; Hiroshi Ohki, Tsuchiura; Isao Yamazaki, Ibaraki; Toshio Kaneko, Katsuta; Hideyuki Horiuchi, Abiko; Shinichi Sakuraba, Tsuchiura; Kaori Yasuda, Maebashi, all of Japan

[73] Assignee: Hitachi, Ltd., Tokyo, Japan

[21] Appl. No.: 404,559

[22] Filed: Sep. 8, 1989

[30] Foreign Application Priority Data

Sep. 19, 1988 [JP] Japan .................. 63-232462

[51] Int. Cl.⁵ .................. G01N 15/00; G01N 33/49
[52] U.S. Cl. .................. 73/864.85; 73/864.21; 73/864.22
[58] Field of Search .................. 422/64, 65, 100; 73/864.81–864.87, 864.91, 864.11–864.35, 864.73, 864.24, 61 R; 436/180

[56] References Cited

U.S. PATENT DOCUMENTS

| | | | |
|---|---|---|---|
| 3,523,733 | 8/1970 | Kling et al. | 73/61 R X |
| 3,583,230 | 6/1971 | Patterson | 73/864.85 |
| 3,604,268 | 9/1971 | Hrdina | 73/864.85 |
| 3,639,830 | 2/1972 | Harnoncourt | 324/450 |
| 4,290,011 | 9/1981 | Berg et al. | 324/71.1 |
| 4,367,043 | 1/1983 | Sweet et al. | 356/338 |
| 4,564,803 | 1/1986 | Loren et al. | 324/71.1 |
| 4,781,459 | 11/1988 | Suzuki | 356/73 X |
| 4,914,966 | 4/1990 | White, Jr. et al. | 73/864.81 X |
| 4,917,494 | 4/1990 | Poole et al. | 356/335 |

FOREIGN PATENT DOCUMENTS

| | | | |
|---|---|---|---|
| 253519 | 1/1988 | European Pat. Off. | 73/864.85 |
| 35250 | 3/1980 | Japan | 73/61 R |
| 196440 | 11/1984 | Japan | 73/864.21 |
| 1-18746 | 5/1989 | Japan | 73/61 R |
| 2071317 | 9/1981 | United Kingdom | 73/864.22 |
| 2075672 | 11/1981 | United Kingdom | 73/864.22 |

*Primary Examiner*—Tom Noland
*Attorney, Agent, or Firm*—Antonelli, Terry, Stout & Kraus

[57] ABSTRACT

Particles contained in a liquid sample are analyzed by moving the particles along a detection passage past a detector using a liquid flow in the detection passage. To reduce the time required for analysis of each sample, the sample is delivered at an input location at the upstream end of the detection passage by movement of a movable container carrying the sample to the input location. Immediately after the commencement of the delivery of the liquid sample, liquid flow is caused to occur in the detection passage. Washing liquid is supplied to the input location by a liquid supplier different from the movable container which carries the sample.

22 Claims, 12 Drawing Sheets

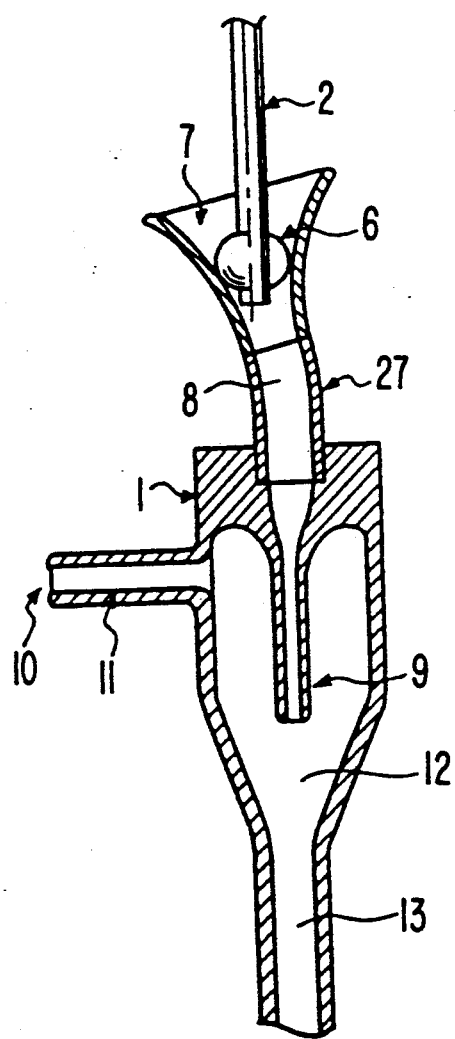
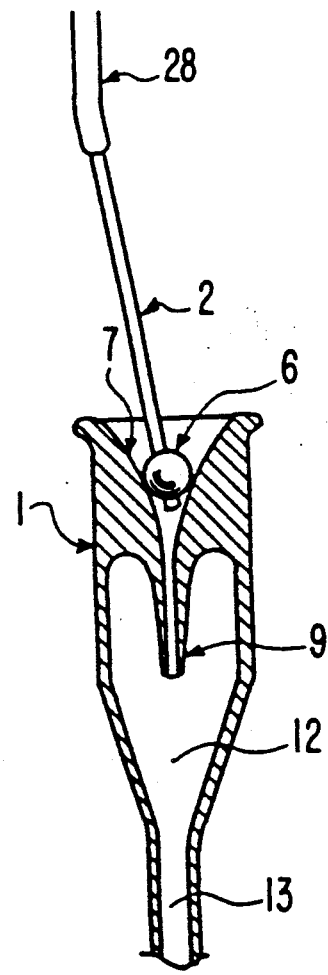
FIG. 3
FIG. 4

FIG. 11
FIG. 12
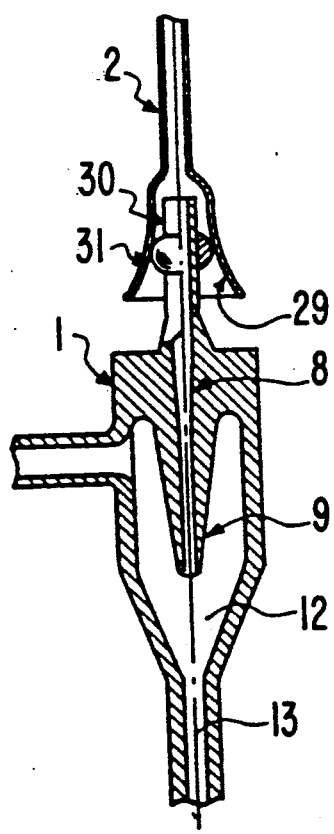
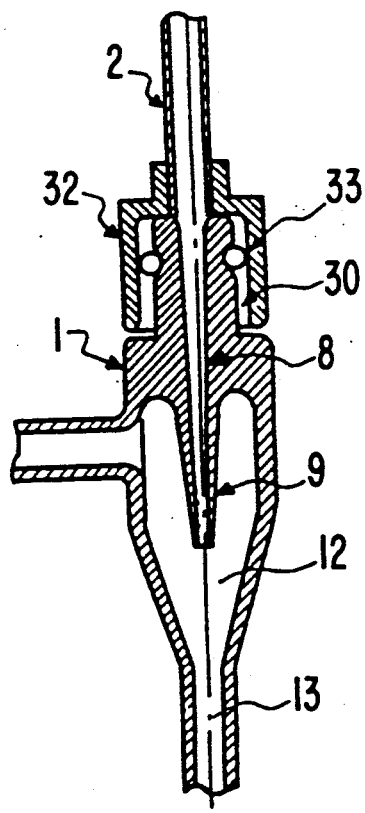

ANALYZING SYSTEM USING SHEATH FLOW OF SAMPLE

BACKGROUND OF THE INVENTION

1. Field of the Invention

This invention relates to a method and apparatus for the analysis of particles in liquid samples, and also to flow cells and other devices for use in the method and apparatus. Particularly the invention is concerned with method and apparatus in which the liquid sample is passed by liquid flow along a detection passage past a detector, for example, a detector using a laser beam. One particular application of the invention is in the analysis of blood cells by counting them to establish their concentration in a particular sample, and the discussion which follows in this specification will mainly be concerned with this use. However, the invention is not limited to this use, and other analyses may be carried out, as mentioned below.

2. Description of the Prior Art

Medical diagnosis requires analysis of blood samples to determine the blood cell concentration, for example, the white blood cell content. This is done by counting the number of blood cells in a sample. The analyzed sample may be a liquid prepared by treatment, including dilution, of the blood. One known form of blood cell analyzer uses an image processing technique, in which cells in a photograph of the sample are recognised and counted. Although this technique is precise, it is slow.

Recently, new blood cell analyzers using a flow technique have been developed. The sample is passed quickly as a thin stream through a laser detector, which counts the cells. Analysis is very quick, for example 10,000 cells per second. Two forms of detection of the cells are used, one based on the scattered light whose intensity depends on the cell size, and the other using fluorescence of a dye which is excited by the laser. The intensity depends upon the cell type.

Some devices using this flow technique are on the market, and one is disclosed in JP-A-60-97241. In these known devices, the flow in the capillary detection passage past the detector is of the type known as sheath flow, in which a carrying liquid which undergoes laminar flow and is, for example, saline solution, entrains the sample as a thin stream, which may even be discontinuous, in the carrying liquid. The sample emerges from a nozzle at a central region of a flow passage for the carrying liquid which narrows towards the detection region. Thus the speed of the carrying liquid increases, and the entrained sample stream becomes thinner. Typically, the width of the stream exiting from the nozzle is of the order of 200 microns, and at the capillary detection region the width of the stream is 10 to 20 microns. The width of the capillary itself may typically be 300 microns square. Thus in the detection region, in the case of a blood sample, the blood cells pass one by one.

The present applicants have developed new forms of sheath flow cells for use in such detection apparatus, employing microfabrication techniques disclosed in EP-A-286088, EP-A-288029 and EP-A-294701. In these flow cells the detection passage has a flat shape, rather than a square cross section, but the same principle of a thin sample stream in laminar flow applies. These new sheath flow cells have particularly low pressure drop, and are further discussed in the paper "Flat flow chambers with low pressure loss" given at the FLUCOME Conference, Sheffield, UK, 1988, by H. Ohki, R. Miyake, I. Yamazaki and T. Kaneko.

The present invention is concerned with the supply of the sample to the flow cell and certain aspects of the design of the flow cell, and is applicable to the flow cells of the prior art discussed above. The principles of blood cell analysis, and other kinds of analysis, and of sheath flow are already known and need not be described in detail here.

In the apparatus shown in JP-A-60-97241, a blood sample of predetermined amount is given a pretreatment involving dilution to make it suitable as a sample fluid for analysis. Other pretreatments may be carried out, for example, mixing with hemolysis solution and dyeing solution. After such treatment, the sample is passed through fixed tubes to the flow cell at which the analysis by detection of the cells is carried out. A blood sample may be split into two samples for analysis, one for the counting of the red blood cells and the other for the counting of the white blood cells. The requirements of this pretreatment process mean that the tubing and its associated valves and pumps is complicated, and the length of the flow path for the sample before it reaches the detector is relatively long.

Of course, the blood samples from different patients must be kept rigorously separate and the parts of the apparatus contacted by a sample must be washed between analysis of different samples. In the known apparatus, a sample is conveyed from the last pretreatment stage to the flow cell along the tubing by holding the front and rear ends of the sample with transport fluid. Inevitably, diffusion occurs at the front and rear boundaries of the sample, so that considerable time is required for a uniform concentration of the sample to reach the detector. This reduces the rate at which samples can be processed.

A second problem arises from the need to keep the samples separate in the apparatus, and to wash the parts of the apparatus contacted by the samples. In the known apparatus, a single sample is subjected to the dilution process, in a dilution tank, and therefore the processing speed may be determined by the time taken for the dilution treatment in the tank and the subsequent washing of the tank with clean fluid.

SUMMARY OF THE INVENTION

One object of the present invention is to make it possible to increase the sample processing rate in the analysis of particles in liquid samples using liquid flow past a detector. Another object is to reduce the amount of sample that may be required.

In one aspect, the invention provides a method of analyzing particles contained in a liquid sample by moving the particles along a detection passage past a detector by means of a liquid flow in said passage. The method is characterized by the steps of (a) delivering said liquid sample containing the particles at an input location at the upstream end of said passage by movement of a movable container carrying said sample to said input location, and (b) immediately after commencement of the delivery of the liquid sample to the input location by the movable container, causing said liquid flow to occur in said passage so as to move the particles from the input location past said detector and analyzing the particles by means of the detector. The sample may commence movement along the detection passage while still being delivered at the input location, or after delivery is completed.

The invention preferably includes the step of supplying washing liquid to said input location by means different from said container which carries the sample. Preferably the flow of the sample in said passage is by sheath flow in which a flowing carrying liquid entrains the liquid sample as a thin stream in the carrying liquid. In this case, the carrying liquid may form said washing liquid for the input location. Washing of the movable container, which may be a pipette, is preferably independent of the washing of the input location.

The method may include holding a plurality of liquid samples simultaneously in a plurality of holding containers prior to the analysis of the particles in each, and sequentially transferring the samples to the input location of said detection passage by means of the movable carrier. In this case the samples may be simultaneously treated while they are held in the holding containers to prepare them for the analysis.

Where the movable container is in the form of a tube containing said sample, the tube may make sealing engagement with the input location, and while this sealing engagement is maintained, pressure which may be suction, is applied to said sample in said tube to deliver it into the input location.

In this invention, suction pressure may be applied to the detection passage to cause said liquid flow to occur in said detection passage so as to move the particles past the detector.

The invention further provides apparatus for analyzing particles contained in a liquid sample, comprising
(i) a detector for the particles,
(ii) a detection passage for liquid flow extending past said detector, so that said particles passing along said passage are detected by said detector for analysis,
(iii) an input location for the liquid sample at the upstream end of said passage,
(iv) means for causing said liquid flow along said passage so as to move the liquid sample from said input location, and
(v) at least one liquid sample holder. The apparatus is characterized by
(vi) a movable container for carrying the liquid sample to the input location from said sample holder, by movement of the container relative to the input location.

Preferably the apparatus includes means, different from the movable container, for supplying washing liquid to said input location.

The apparatus may include sealing means for temporarily sealing the movable container to the input location while delivery of the sample at the input location takes place. The sealing means may comprise a resilient seal mounted on said tube.

In another aspect, the invention provides a pipette for use in transferring a liquid sample from a sample holder to an input location of a detection passage of a particle analyzer. The pipette comprises a tube for containing the liquid sample having an inside diameter of not more than 1 mm and a resilient seal mounted on the tube for forming sealing engagement with the input location.

The flow cell may have input chamber at the input end of the detection passage, having an inlet for delivery of the sample to the chamber, a first outlet port connecting directly to the detection passage and a second outlet port for outflow of washing liquid. The movable container may have a discharge location in said chamber downstream of the second outlet. Suction means may be connected to the second outlet port for sucking washing liquid from the input chamber.

In another aspect, the invention provides a flow cell for apparatus for analyzing particles contained in a liquid sample, comprising
(a) a detection passage for flow of liquid,
(b) a sample inlet to said detection passage adapted to receive an outlet nozzle of a sample delivery container,
(c) a resilient seal extending around said sample inlet to seal against the sample delivery container,
(d) means to supply carrying liquid to said detection passage so as to establish sheath flow in said detection passage in which the flowing carrying liquid entrains the liquid sample as a thin stream in the carrying liquid.

In the apparatus of the invention, means for supplying carrying liquid to the detection passage so as to establish sheath flow may comprise at least one carrying liquid inlet of the flow cell connected to the detection passage and a connector external to the flow cell for supplying carrying liquid which is adapted to be sealingly and detachably engaged with said carrying liquid inlet. The connector may be arranged to move in conjunction with the movable container whereby its engagement with the carrying liquid inlet is established upon movement of the movable container with a sample to the flow cell.

In a flow cell of the invention, there may be a sample inlet to the detection passage adapted to receive delivery of said sample from the movable sample delivery container, said sample inlet including a deformable mouth portion for engagement with the sample delivery container.

BRIEF INTRODUCTION OF THE DRAWINGS

Embodiments of the invention are described below by way of non-limitative example, with reference to the accompanying drawings, in which:

FIG. 3 is a sectional view of a modified form of the flow cell of FIG. 2;

FIG. 4 is a sectional view of another modified form of the flow cell and pipette of FIG. 2;

FIG. 11 and FIG. 12 are further partial sectional views of flow cells and pipette arrangements embodying the invention;

DESCRIPTION OF THE PREFERRED EMBODIMENTS

Figure 1:
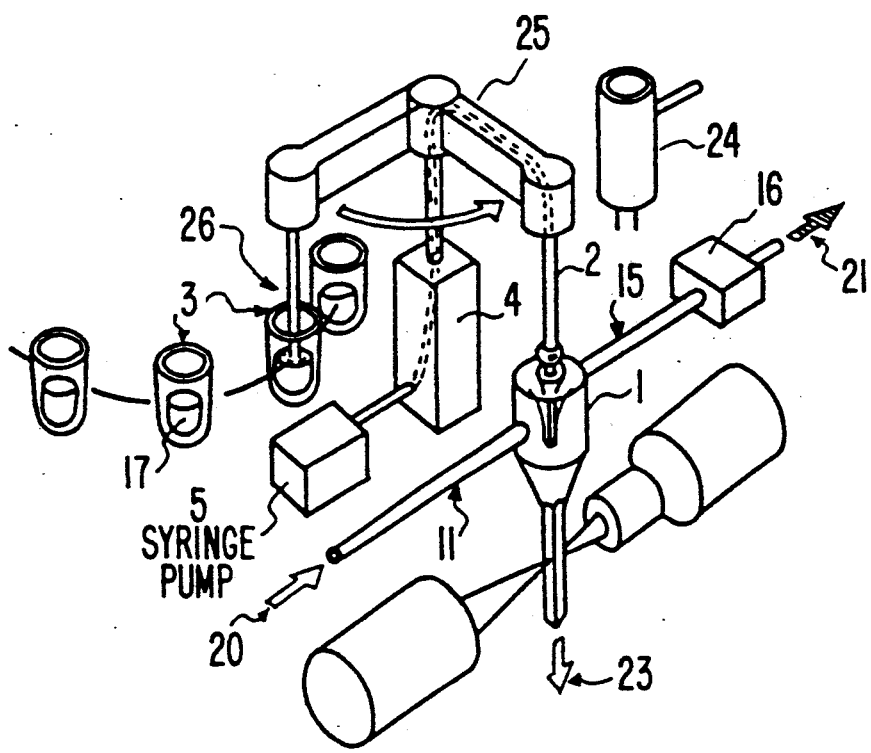
FIG. 1 is a diagrammatic perspective view of a particle analysis apparatus embodying the invention.

In the figures of the many different embodiments described below, the same reference numerals are used for corresponding parts, which will not be described fully for each embodiment.

Referring to FIG. 1, the apparatus has a flow cell 1 to which are connected a pipe 11 for supplying the carrying liquid for sheath flow and an outlet pipe 15 for discharge of unused sample and washing fluid. A valve 16 opens and closes the passage through the pipe 15. A pipette 2 is mounted on an arm 25 to swing about a vertical axis and to be vertically moved with vertical movement of the arm 25. In FIG. 1 the pipette 2 is shown in two alternative positions, i.e. a discharge position at the cell 1 and a take-up position at a sample holder 3. The arm 25 is driven by a pipette driving device 4. Pick-up and discharge of liquid from the pipette is controlled by a syringe pump 5 through tubing.

The arm 25 is rotatable further to a washing station 24 for the pipette 2.

The apparatus has a plurality of sample holding containers 3 which are rotated to the sample pick-up position 26 in turn. See FIG. 10 for details of one possible arrangement of the sample supply apparatus.

Figure 2:
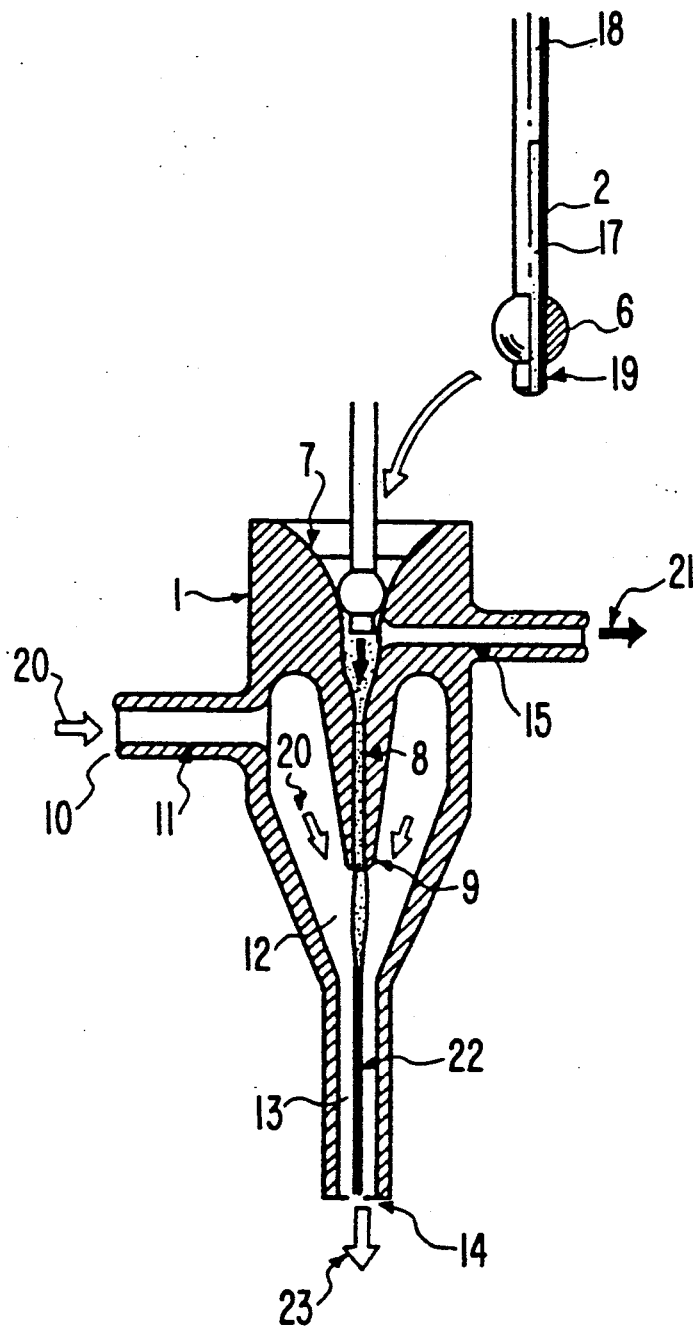
FIG. 2 is a sectional view of the flow cell of the apparatus of FIG. 1 together with the pipette.

FIG. 2 shows in detail the connection of the pipette 2 to the flow cell 1 and the structure of the flow cell 1. The pipette is of inside diameter of 400 microns. The pipette 2 has a ring seal in the shape of a ball 6 on its exterior surface close to its lower end 19. The ball 6 is of resilient material, for example, rubber. FIG. 2 indicates that the pipette contains a sample fluid 17 and a transport fluid 18 which is used to move the sample fluid 17 into and out of the pipette.

As FIG. 2 also shows, the pipette 2 is received by an upwardly open bell-shaped mouth 7 of the flow cell 1. The mouth 7 narrows downwardly into a narrow passage 8 which ends at a nozzle 9. The mouth 7 and passage 8 constitute the input location of the flow cell 1. The nozzle 9 opens into a downwardly narrowing portion 12 of the detection passage of the flow cell. The carrying liquid for the sheath flow enters the upstream end of this narrowing portion 9 via the inlet 10 represented as part of the pipe 11. The flow of the carrying liquid is indicated by arrows 20. The narrow end of the narrowing portion 12 connects with the capillary detection portion 13 of constant cross section, which ends at an outlet 14, from which the discharge is represented by arrow 23. The flow of carrying liquid entrains the sample liquid emerging from the nozzle 9, which is accelerated by the contracting laminar flow of the carrier liquid in the portion 12 and forms a thin stream 22 in the detection portion 13.

FIG. 1 illustrates how a detector is mounted to detect the passage of particles in the thin stream 22 in the detection portion 13 of the cell 1. As mentioned above, the principles of such sheath flow and the detection of particles in it is already known and need not be discussed further.

FIG. 2 shows that the ball 6 forms a seal in the mouth 7 of the cell 1 when the pipette is inserted into the mouth 7. The connection of the pipe 15 into the mouth 7 is below, i.e. downstream of, the sealing point of the ball 6 in the mouth 7, in this embodiment.

The operation of the apparatus of FIGS. 1 and 2 will now be described. Liquid samples to be analysed are stored in each of the sample containers 3 and are sent to the sample sucking position 26 one at a time. The pipette 2 is lowered by the device 4 into the container 3 so that its tip is immersed in the sample liquid, and then a fixed amount of the sample 17 is sucked into the pipette 2 by the pum 5. The pipette 2 is raised and rotated into the position above the flow cell 1 and is slowly lowered. The carrying fluid 20 for sheath flow is continuously supplied to the flow cell and discharges through the outlet 14 via the capillary portion 13 and is also discharged through the discharge pipe 15 having passed by reverse flow through the nozzle 9 and the passage 8, in order to wash these parts. At this time the valve 16 is open. In this way, any remaining traces of the previous sample analysed have been completely removed by the carrying liquid.

The descending pipette 2 centers itself in the mouth 7 and the circumference of the ball 6 seals closely to the inner surface of the mouth 7 over its entire periphery. The downward force exerted by the driving device 4 is adjusted to achieve this sealing suitably. The valve 16 is closed immediately before close sealing of the ball 6 takes place so that the upper surface of the carrying fluid in the mouth 7 rises. Therefore, as the ball 6 becomes tightly sealed to the mouth 7 below the level of the surface of the carrying liquid, no air bubbles are formed in the passage 8. After sealing of the ball 6, the pump 5 starts to cause discharge of the sample 17 at a predetermined rate. The sample is discharged from the nozzle 9 into the contracting region 12 and the sheath flow 22 of the sample is formed in the capillary region 13.

After a predetermined amount or all of the sample fluid 17 has been pushed out of the pipette 2, the pipette is raised and removed from the inlet 7. At the same time, the valve 16 is opened and any residual fluid 17 is completely discharged via the discharge pipe 15. The pipette 2 is rotated and lowered into the washing tank 24 and thoroughly washed out by fluid discharge by the pump 5 and by washing water circulating in the washing tank, to wash the exterior of the pipette.

Figure 15:
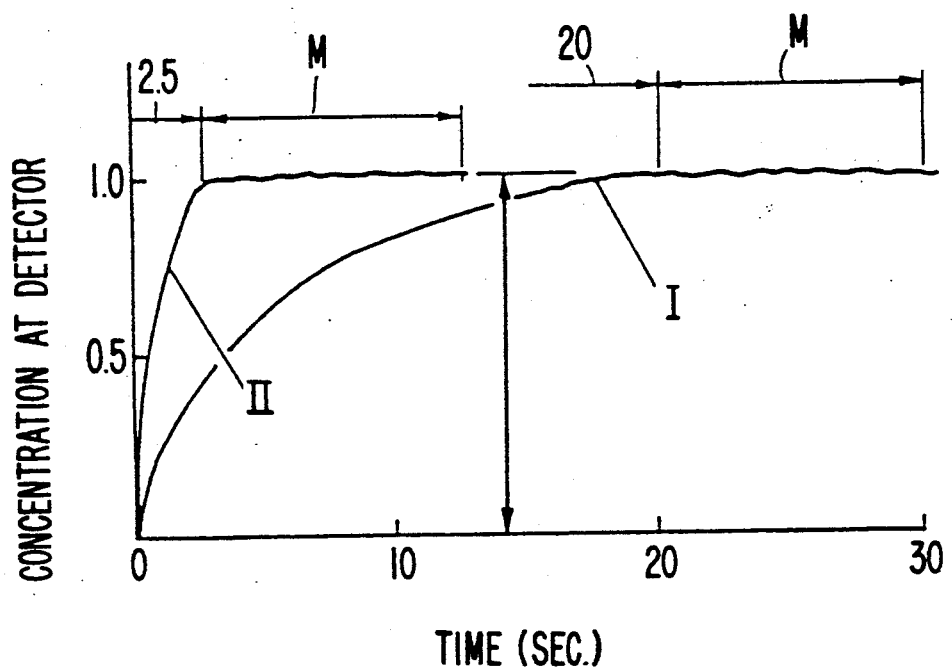
FIG. 15 is a graph illustrating the concentration rise at the detector against time.

The advantages of this analysis apparatus are as follows. Firstly, a plurality of samples may be simultaneously stored in the sample containers 3 and may be held in readiness for analysis sequentially by the flow cell 1 and the detector. Furthermore, as described below, the samples may undergo preparation for analysis while in the containers 3, simultaneously. The pipette 2 moves the sample rapidly from the container 3 into the flow cell 1, and the sample is discharged into the flow cell close to the detection portion 13 immediately before flow takes place through the detection portion 13. Therefore, the time between passage of two adjacent samples in the sequence through the flow cell 1 is determined by the time taken by the movable pipette 2 to collect samples, deliver them at the flow cell and be washed. Washing of the flow cell takes place between delivery of the samples. There is no delay while long tubing is washed or the sample containers 3 are washed. Furthermore, the use of a transport fluid 18 for only sucking up and then after a short interval delivering the sample 17 means that diffusion does not occur at the leading portion of the sample, i.e. the portion which first enters the detector region 13. Consequently, as illustrated by FIG. 15 described below, the rise of the concentration of the sample in the detector portion 13 to the steady state level is much quicker than in the prior art apparatus described above where the sample travels through long tubing to the flow cell.

The various samples held in the containers 3 may relate to the same original blood sample, and be prepared for different analysis in the flow cell, if the detector or detectors used so permit. Alternatively, there may be a plurality of samples from different patients, prepared for the same analysis in the flow cell.

It is particularly to be noted that the arrangement of the outlet 15 from the sample input location permits very rapid and efficient washing of the residual sample from the flow cell.

The sealing of the ball 6 and the inlet 7 of the flow cell avoids any leakage of sample, so that if desired the whole volume of the sample is passed into the capillary region 13. This means that substantially all the particles, e.g. blood cells, in the sample can be counted by the detector. If the dilution ratio of the sample, relative to the original blood sample, is known, the concentration of blood cells in the original sample can be calculated.

The volume of the passage 8 is small. For example, it may be less than 5 microliters, so that the sample 17 discharged from the pipette 2 rapidly reaches the nozzle 9. This minimizes diffusion at the front and rear of the sample 17. Thus a uniform concentration of particles in the detector region 13 is rapidly achieved and measurement time is minimized.

The use of a pipette to transfer the sample to the flow cell permits accurate delivery of predetermined quantities, e.g. 5 to 10 microliters.

This embodiment has been described particularly for counting of blood cell particles, but the invention is applicable to particle counting or analysis of particles in other ways generally. Thus it may be used for particle size detection, e.g. in analysis of liquid purity. It may be used to analyze, e.g. by counting, other biological cells, such as bacteria, as well as non-biological particles.

FIG. 3 shows an embodiment in which the upper part of the passage 8 at the input location of the cell 1 is a flexible tube 27 of silicone rubber, connecting to the rigid mouth 7. The tube 27 can bend, so that the mouth 7 aligns with the descending position of the pipette 2 even if the pipette is lowered off the normal center line of the mouth 7. This permits rapid insertion of the pipette 2 into the mouth.

FIG. 4 shows an embodiment in which the pipette 2 includes a flexible portion 28 of silicone rubber, above the lowermost rigid portion. Again, the pipette 2 can rapidly align itself with the center of the mouth 7 as it descends. Thus any positional inaccuracy of the pipette 2 is corrected, which enables rapid operation.

Figure 5:
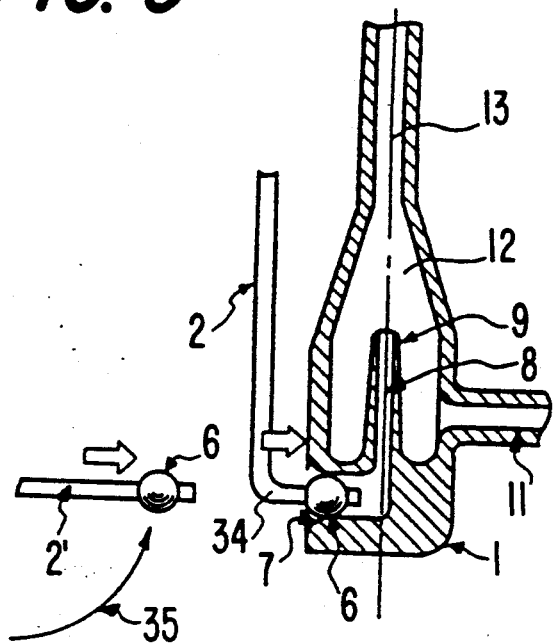
FIG. 5 is a partial sectional view of a further form of flow cell useful in the invention.

In FIG. 5, the end portion of the pipette 2 has a bend 34 so that its tip extends horizontally, for a few mm at most. The mouth 7 receiving the pipette tube is also horizontal, and the orientation of the flow cell is upside down compared with that of FIG. 2. Thus the flow of the carrying fluid and the sample is upwardly, and the pipette is moved horizontally in order to bring its discharge end into the mouth 7.

FIG. 5 also shows an alternative form of pipette 2', which, after having sucked the sample upwardly from a sample holder 3 is rotated as indicated by arrow 35 to a horizontal position, and then moved horizontally into the horizontal mouth 7 of the flow cell 1. This avoids the need for a bend 34 in the pipette.

In another alternative, the mouth 7 opens downwardly, and the discharge pipe 15 of FIG. 2 is present.

The advantage of these arrangements in which the mouth 7 is horizontal or opens vertically downwards and the flow through the flow cell is generally upwardly is that any air bubbles which arise in the mouth 7 or in the inlet 11 for the carrying fluid are rapidly discharged upwardly.

Figure 6:
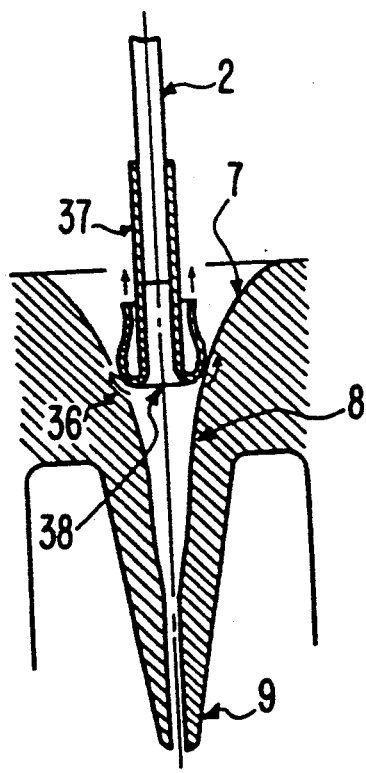
FIG. 6 is a partial sectional view of a further modified form of flow cell and pipette of the invention.

FIG. 6 illustrates a different form of resiliently deformable seal on the pipette 2. A rubber tube 37 grips the rigid portion of the tube 2 a its outlet end, and the tip 38 of the tube 37 is rolled back outwardly. The tube 37 makes sealing connection to the mouth 7 at the bend of this rolled portion 38. When desired, the length of the rolled portion 38 can be increased, i.e. the tube 37 rolled up a little further, as indicated by the arrow 36 by increase of the downward force of the pipette 2. Thus deterioration of the rubber tube 37 caused by reagents in the sample fluids or by repeated operation can be dealt with by supplying a fresh region of surface for contact with the mouth 7, by the rolling up action described above. This improves the maintenance performance of the apparatus.

Figure 7:
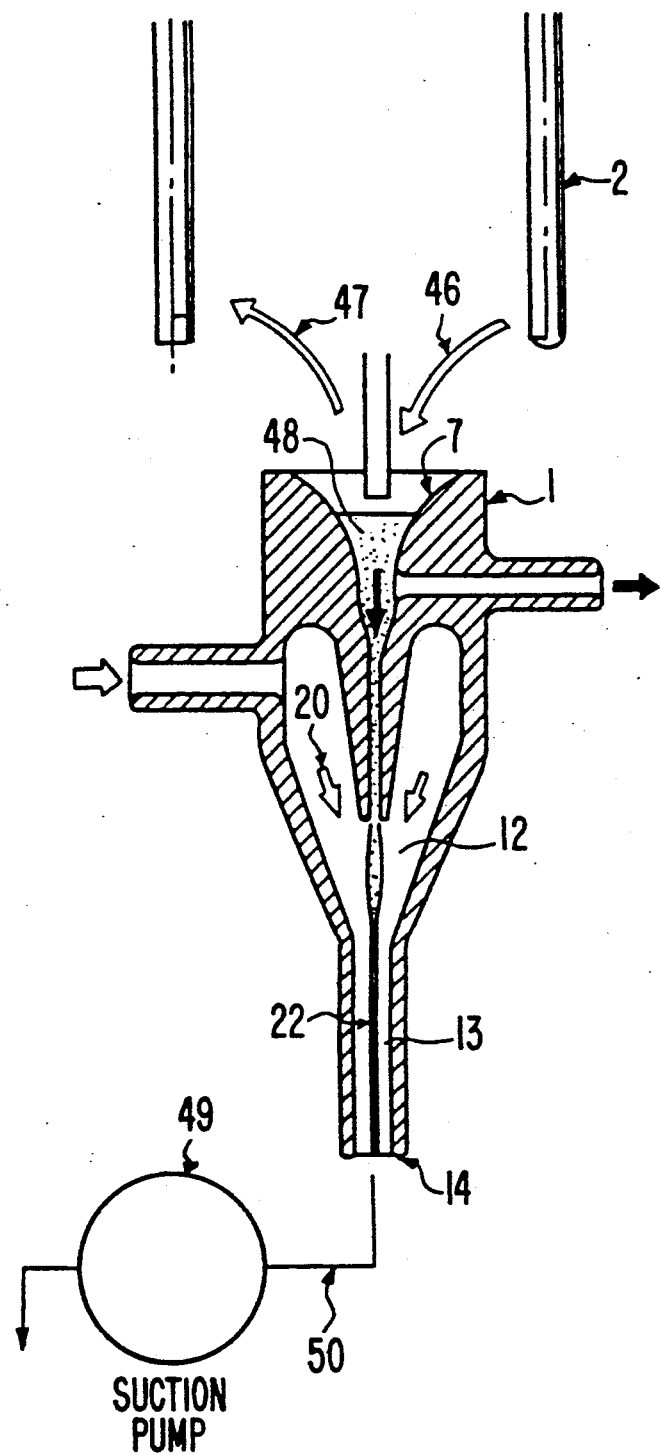
FIG. 7 illustrates part of another analysis apparatus embodying the invention.

In the embodiment of FIG. 7, the discharge port 14 of the flow cell is connected to a suction pump 49 through a pipe 50. The pipette 2 has no resilient seal and makes no contact with the mouth 7. The pipette 2 is moved to a position above the mouth 7 as indicated by the arrow 46 after sucking up the sample 17 and discharges the desired amount of the sample into the mouth 7. Immediately after this discharge, it is moved to the washing tank 24 as indicated by the arrow 47. Meanwhile, in the flow cell 1, the carrying fluid for the sheath flow is sucked through the cell by the suction pump 49, and therefore a negative pressure is formed in the contracting portion 12, and the sample now stored in the input location 7 is discharged from the nozzle 9 to form the sheath flow. This means the pipette 2 does not need to wait at the flow cell 1 while the flow of the sample through the flow cell is performed and can perform other operations, e.g. be washed and collect another sample, during the analysis of the previous sample. Thus the average measurement time can be decreased.

Figure 8:
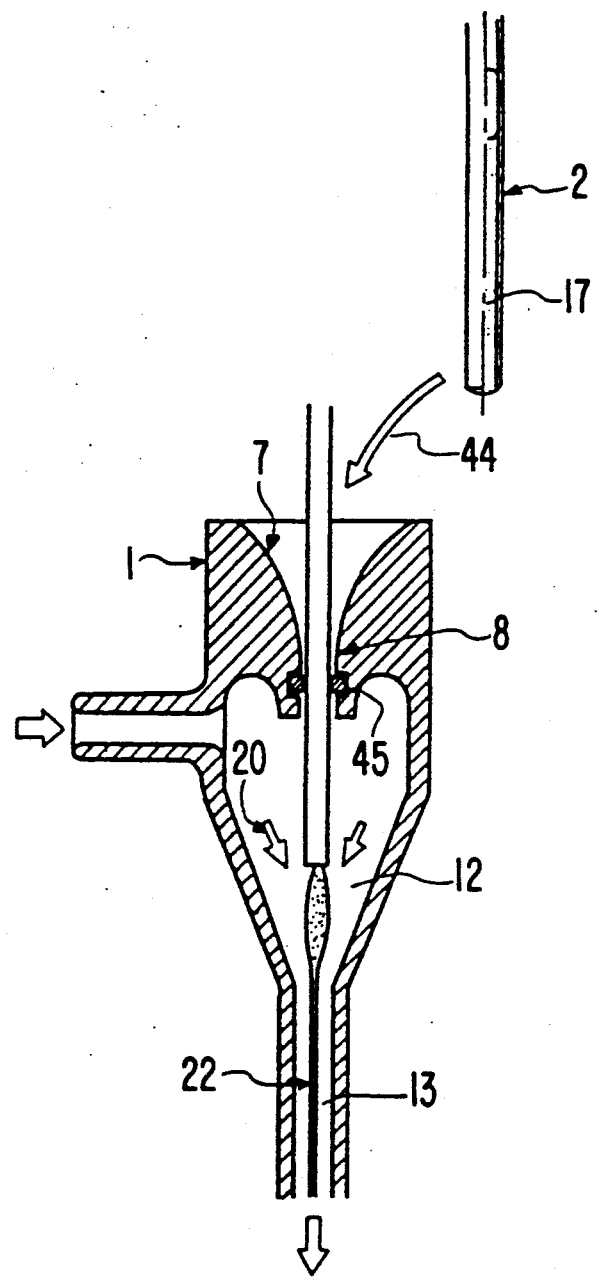
FIG. 8 is a partial sectional view of a further flow cell and pipette arrangement embodying the invention.

In the embodiment of FIG. 8, there is no nozzle 9 for discharge of the sample at the input location. The passage 8 contains a groove around it and a resilient O-ring 45 with an inside diameter slightly smaller than the outside diameter of the pipette tube 2 is lodged in this groove. As FIG. 8 shows, the pipette itself is inserted through the O-ring 45, and forms the nozzle at its outlet end, which is located in the narrowing portion 12 of the cell 1. By reason of the seal of the passage 8 by the O-ring 45, the carrying fluid 20 cannot leak here. In the same way as in the previous embodiments, the sheath flow 22 of the sample is formed at the capillary portion 13. When the desired amount of sample has been discharged from the pipette 2, the pipette is withdrawn from the flow cell 1.

In this embodiment, since the sample liquid 17 is discharged directly into the narrowing portion 12 in the flow cell without passing through any other passageway, the sheath flow of a desired uniform rate of the sample can be achieved extremely rapidly, and the measurement time reduced. Furthermore, by reason of the sheath flow, no part of the flow cell comes into contact with the sample, which reduces the need for washing, and avoids pollution of the flow cell by sample or reagent carry-over.

Figure 9:
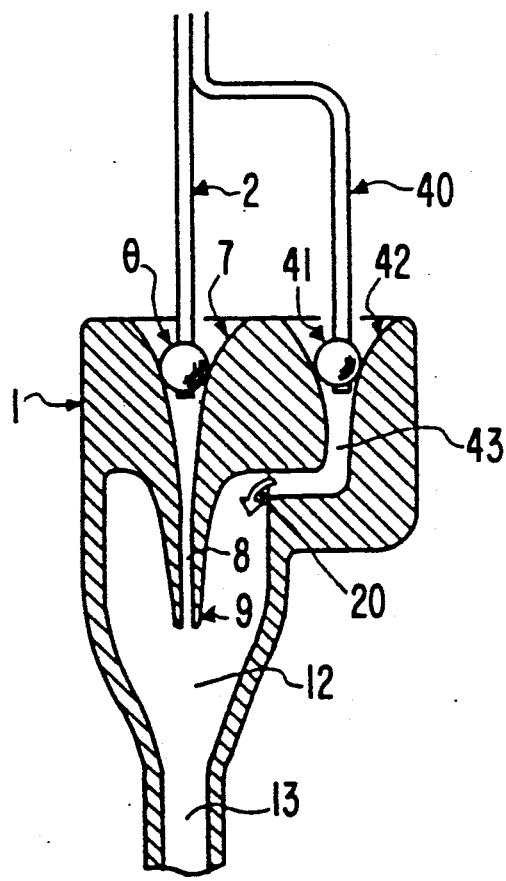
FIG. 9 is a further partial sectional view of an embodiment of flow cell and pipette embodying the invention.

In the embodiment of FIG. 9, the flow cell has an upwardly opening bell-shaped mouth 42 for inlet of the carrying liquid for the sheath flow. A passage 43 connects this inlet 42 with the narrowing portion 12. A movable tube 40 has a ball seal 41 at its lower end, like the pipette tube 2, and makes contact with the mouth 42 in the same way. The two tubes 2 and 40 are joined together so as to move in conjunction, under the action of the driving device 4. The pump for causing discharge of the carrying liquid from the tube 40 is provided. When the connections of the tubes 2 and 40 at the respective mouths 7 and 42 have been made simultaneously, the flow of carrying fluid 20 from the tube 40 is started first, and the flow of sample liquid from the pipette 2 is started a little time later. The carrying liquid may be brought into the tube 40 by sucking it upwardly through its discharge end, i.e. in the manner of a pipette. Carrying liquid specifically chosen for the particular sample in the pipette 2 can thus be quickly and easily simplified. Similarly, if the flow cell is changed, a quick restart is possible. The embodiment also allows a quick change of the flow cell since no fixed connection for the carrying liquid is required. A similar readily detachable connection for the output on the discharge port 14 can easily be arranged, so that there is no fixed connection to the flow cell. The flow cell is then easily exchanged, e.g. when a different detector is employed or for maintenance purposes.

Figure 10:
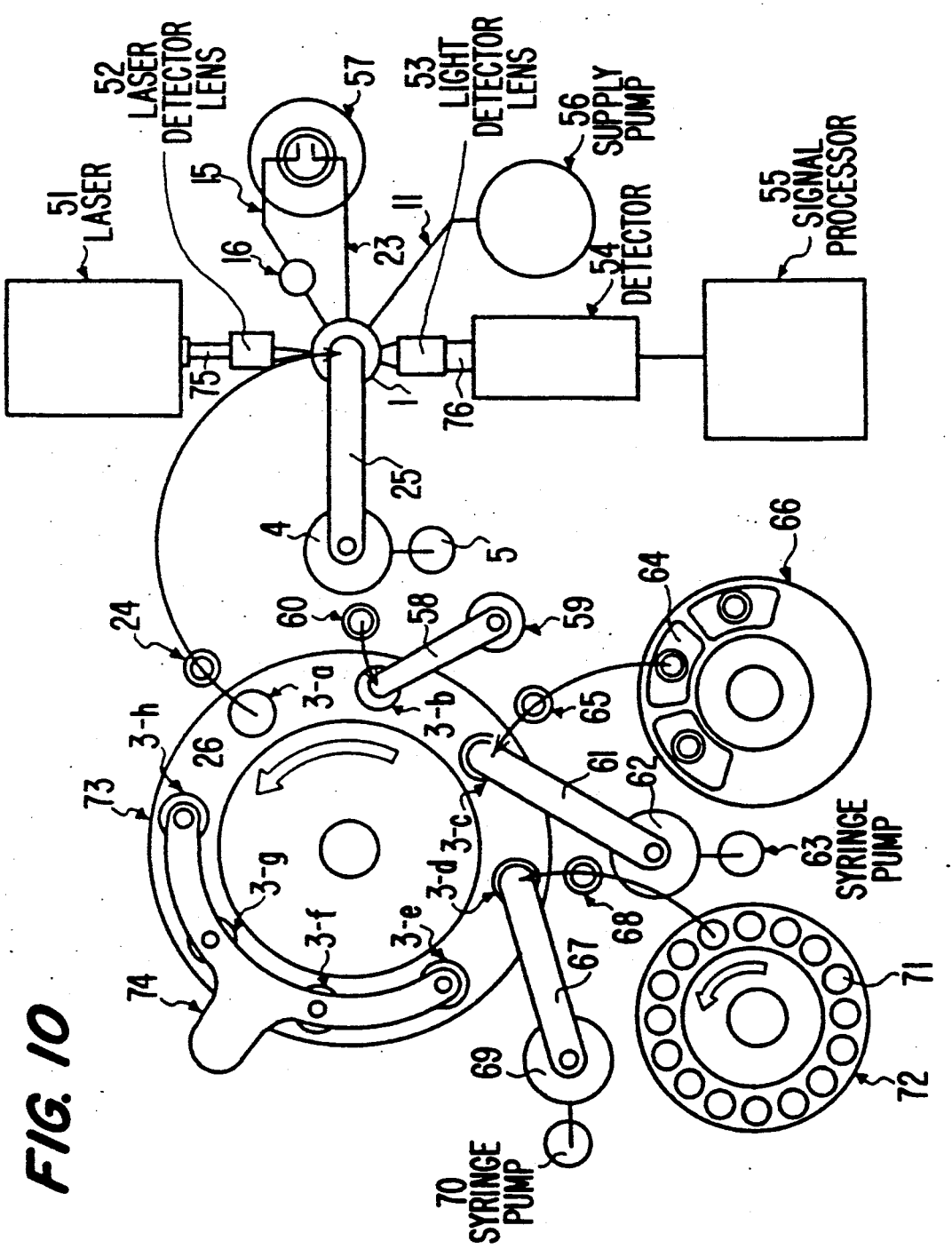
FIG. 10 is a general diagrammatic view of a particle analysis apparatus embodying the invention, similar to that of FIG. 1 and including sample preparation equipment.

FIG. 10 is a general view from above of apparatus embodying the invention, including means for preparing the samples for the particle analysis. A laser source 51 is indicated with a laser condenser lens 52 in front of it, and a fluoresence and scattered light detector lens 53 on the opposite side of the capillary portion of the flow cell 1. A light detector 54 is indicated beyond the lens 53 and a signal processor 55 is connected to the detector 54.

A supply pump 56 for the carrying liquid is indicated, connected to the pipe 11. A tube 23 is shown for discharge of the waste fluid from the port 14 of the flow cell, connecting to a waste fluid bottle 57. Likewise the outlet pipe 15 for washing fluid and residual sample fluid is connected into the bottle 57.

The sample holding containers 3 are mounted with equal spacing at positions 3-a to 3-h around the circumference of a rotatable reaction table 73. The position 3-a is the pick-up position for the pipette 2, which delivers the sample to the analysis cell 1. At the next position 3-b in the clockwise direction around the table 73 is a stirring device consisting of a stirring arm 58 and a washing tank 60 for washing a stirring rod at the tip of the arm 58. The arm 58 is rotated and raised by a device 59.

At the next position 3-c, a reagent supplying device is shown, consisting of a rotatable arm 61 carrying a reagent pipette, with a driving device 62 for the arm and a syringe pump 63 for the pipette. There is a washing tank 65 for the reagent pipette along its arc of movement. Reagent bottles 64 are located around a reagent disc 66, and various reagents can be supplied to the samples by means of the reagent pipette by rotating the disc 66 to bring the desired sample into the position on the arc of movement of the reagent pipette, so that the reagent can be picked up and carried to the sample container.

At the next position 3-d in the clockwise direction around the table 73 is a sample supplying device, for supplying samples to the sample holding containers 3 on the table 73. This sample supplying device has a rotatable arm 67 carrying a sample pipette, with a pipette driving device 69 and syringe pump 70 and a washing tank 68 for this pipette, as for the reagent supplying device and the pipette 2. A large number of sample cups 71 are mounted around the circumference of a sample disc 72, which rotates to bring the samples in turn to the location of the arc of movement of the sample pipette. A washing device 74 for washing the sample containers 3 is shown at the position 3-e to 3-h.

The apparatus of FIG. 10 operates as follows.

The sample pipette is moved to above one of the sample cups 71 by the sample pipette driver 69, is lowered into the sample cup and sucks up a predetermined amount of the sample. The sample pipette then moves to the sample holding container 3 at position 3-d of the reaction table 73 and discharges the predetermined amount of the sample. The sample pipette then moves to the washing tank 68 to be thoroughly washed. The reaction table 73 is rotated, to bring the container at 3-d to the next position 3-c. A predetermined amount of a desired reagent is added by the reagent pipette, which has collected the reagent from a reagent container 64 by an action similar to that of the sample pipette. The reaction table 73 is further rotated to bring the sample container now to the position 3-b. Here the contents of the container are stirred by the stirring device carried by the arm 58, and the desired reaction allowed to take place. Next the container 3 is rotated to the position 3-a, and a predetermined amount of the sample is supplied to the flow cell 1 by the pipette 2 carried by the arm 25. This action is repeated cyclically for each new sample. The cycles overlap, i.e. several samples may undergo treatment simultaneously. If the reaction time required after addition of the reagent at position 3-c and the stirring at position 3-b is longer than the rate at which it is desired to feed samples to the flow cell 1, an additional number of positions, at which the reaction is allowed to take place, can be provided on the reaction table. After the sample has been taken by the pipette 2 to the flow cell 1, the sample holding container is moved to the washing device 74, and surplus sample liquid is removed and the container thoroughly washed.

As already described, the liquid sample supplied to the flow cell 1 is moved along the detection passage past the laser beam of the detector, and as desired the beam of scattered light and fluorescent light 76 is generated from the laser beam 75. The light 76 is captured by the detector 54 and desired information about the relevant particles is obtained at the signal processor 55.

The various pipettes and the rotating carriers 66, 72 and 73 are all controlled in conjunction with the flow cell 1 by suitable microprocessor technology.

The samples are not conveyed by continuous tubes from the input to the apparatus to the reaction vessels and the flow cell. Thus there is no problem of pollution of such tubes by sample or reagent carry over. The absolute quantity of the samples and reagents required can be kept to the minimum. A plurality of samples can be undergoing preparation for analysis in the flow cell 1 simultaneously, and with great rapidity. This permits a very high rate of sample treatment, per hour.

In the embodiment of FIG. 11, as compared with that of FIG. 2, the pipette mouth is a downwardly opening bell shape 29 while the passage 8 has an upward extension 30 of cylindrical shape carrying on its outer surface a rubber ring seal 31 of ball shape. Connection between the pipette and the passage 8 is made by bringing the mouth 29 of the pipette downwardly into contact with the ball 31. This provides a precise seal of the pipette to the flow cell.

In the embodiment of FIG. 12, the end of the pipette 2 has the shape of a widened cylinder 32. The passage 8 has an upward extension 30, of cylindrical shape and having a circumferential groove in its outer surface, in which an O-ring 33 is located. To form a connection with the pipette 2, the projection 30 is received in the cylindrical portion 32 of the pipette, and a good seal is achieved by the O-ring 8. With this embodiment, the connection force of the pipette 2 to the flow cell 1 may be strong enough to allow the flow cell to be picked up by upward movement of the pipette 2, which allows the flow cell 1 to be lifted out for replacement.

Figure 13:
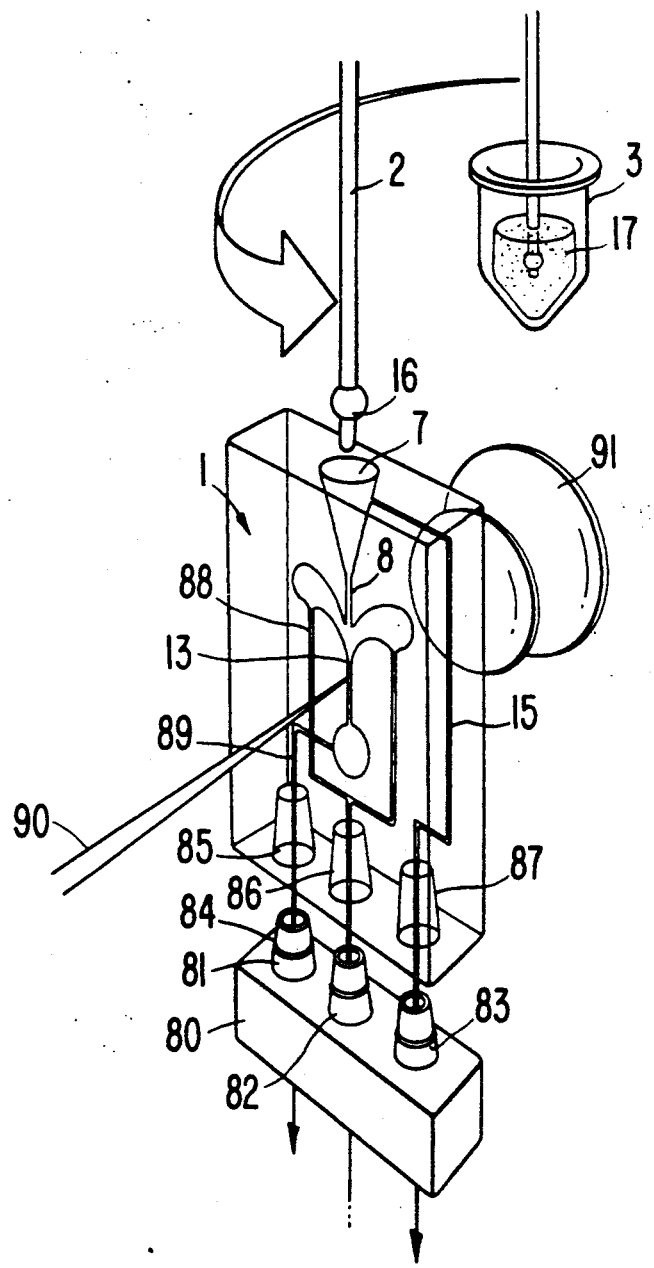
FIG. 13 is a diagrammatic perspective view of a further flow cell of the flat type, embodying the present invention.
Figure 14:
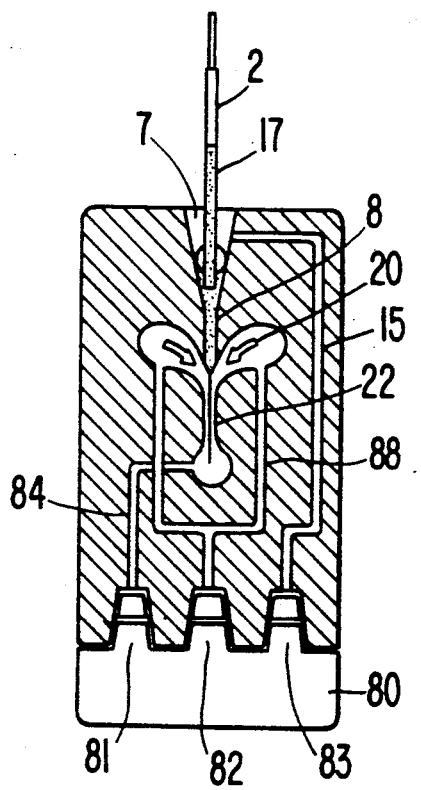
FIG. 14 is a diagrammatic sectional view of the flow cell of FIG. 13.

FIGS. 13 and 14 show a flat flow cell 1 which can be made in the way described in EP-A-286088, EP-A288029 and EP-A-294701. The pipette 2 used with this flow cell 1 is the same as in FIG. 2 and carries a ball seal 16, which makes sealing contact, as shown in FIG. 14, with a conical inlet mouth 7 of the cell, in the same manner as described above. As FIG. 14 shows, however, the outlet passage 15 for residual sample and washing fluid opens to the mouth 7 above, i.e. upstream of, the sealing location of the ball 16, which contributes to improved washing of the mouth 7.

At the bottom of the cell 1 of FIG. 13 there are three part conical recesses 85,86,87 which mate with corresponding tapering connections 81,82,83 on a connector block 80. The connections 81,82,83 each carry an O-ring 84 which makes sealing engagement with the recesses 85,86,87. There is thus achieved a plug type connection at each of the recesses 85,86,87. A passage 89 for the discharge of an analysed sample and the carrying liquid connects into the recess 85 for discharge via the connection 81. The connection 82 and recess 86 connect to passages 88 for the incoming carrying liquid for the sheath flow through the detection portion 13. The connection 83 and recess 87 connect with the outlet passage 15 for the washing fluid and residual sample from the mouth 7. The fluid passing along the outlet passage 15 is sucked through the connection 83.

The analysing light beam 90 and detector 91 are indicated in FIG. 13.

By reason of the plug-type connections at the lower end of the flow cell 1 and the use of the moveable pipette 2 to bring the sample liquid to the flow cell 1, the flow cell is very easily removed and replaced, e.g. when it is desired to change the type of analysis being performed by the apparatus.

Referring now to FIG. 15, this demonstrates the improved processing speed of samples which can be obtained with the present invention. The time zero of the horizontal axis represents the time at which the first portion of the sample fluid reaches the detection point in the flow cell, and the curves I and II indicate the rise of concentration of the detector to the steady state at which an approximately uniform concentration is present. This uniform concentration is given the value 1.0. The measuring time M required at this steady state is, in this example, about 10 seconds. The curve I is a typical result achieved for an analysis apparatus in which the sample is moved to the flow cell through a fixed tubing system, and it can be seen that the time taken to achieve the steady state at the detector is about 20 seconds. This applies for a tubing of length about 200 to 300 mm. In contrast, using apparatus of the present invention as shown in FIG. 1, the curve II is obtained, in which the rise to the steady state occupies about 2.5 seconds. Not only is there a great reduction in the total time required to process the sample in the flow cell, but also the required amount of each sample is reduced, compared with the prior art apparatus.

What is claimed is:

1. A method of analyzing particles contained in at least one liquid sample by moving the particles along a detection passage past a detector by means of a liquid flow in said passage, which method includes the steps of
   (a) delivering one liquid sample, of said at least one liquid sample, containing the particles to an input location at an upstream end of said detection passage by moving a movable container carrying said sample to said input location, and forming a seal between the movable container and said input location, the input location being immediately upstream of the detection passage so as to be directly connected thereto, wherein said movable container has an output nozzle for said one liquid sample, the one liquid sample being delivered to said input location from said movable container through said output nozzle,
   (b) supplying a carrying liquid to said detection passage so as to cause sheath flow in said detection passage in which the flowing carrying liquid entrains the one liquid sample as a thin stream in the carrying liquid, whereby the sample is carried past the detector in said sheath flow,
   (c) immediately after commencement of the delivery of the one liquid sample to the input location by the movable container, causing said liquid flow to occur in said detection passage so as to move the particles from the input location past said detector and analyzing the particles by means of the detector, and
   (d) supplying washing liquid to said input location by means different from said movable container which carries the sample.

2. A method according to claim 1 wherein said carrying liquid forms said washing liquid for the input location.

3. A method according to claim 1 wherein a plurality of liquid samples respectively containing particles, in a plurality of sample holders, are sequentially carried by said pipette to said input location for analysis.

4. A method according to claim 3 wherein one of the plurality of liquid samples is carried to said input location, the steps (a), (b), (c) and (d) are performed on said one of the plurality of liquid samples, and, thereafter, a following one of the plurality of liquid samples is carried to said input location and the steps (a), (b), and (c) and (d) are performed on said following one of the plurality of liquid samples.

5. A method according to claim 3 wherein said plurality of liquid samples are held in a plurality of holding containers, respectively, prior to carrying a respective liquid sample to said input location for analysis.

6. A method according to claim 1 including the step of washing said movable container independently of the washing of the input location.

7. A method according to claim 1 wherein said moving container is a pipette tube.

8. A method according to claim 1 wherein said input location has a resilient seal which seals against said moving container.

9. A method according to claim 1 wherein the detection passage has the upstream end thereof in a flow cell, the input location being immediately upstream of the upstream end of the detection passage.

10. Apparatus according to claim 9 wherein said pipette comprises a tube for containing said liquid sample, said tube having an inside diameter of not more than 1 mm and a resilient seal mounted on said tube for forming sealing engagement with said input location.

11. Apparatus for analyzing particles contained in a liquid sample, comprising
   (i) a detector for the particles,
   (ii) a detection passage for liquid flow extending past said detector, so that said particles passing along said detection passage are detected by said detector for analysis, said detection passage having an input end at which said sample enters the passage,
   (iii) an input chamber at said input end of said passage, having an inlet for delivery of said sample to said chamber, a first output port connecting directly to said detection passage and a second outlet port for outflow of washing liquid,
   (iv) means for causing liquid flow along said detection passage so as to move the liquid sample from said input chamber past said detector, the means for causing liquid flow including a means for causing sheath flow in the detection passage in which a carrying liquid entrains the liquid sample as a thin stream in the carrying liquid, to carry the liquid sample past the detector in sheath flow, and
   (v) means for supplying said washing liquid to said input chamber.

12. Apparatus according to claim 11 further having a movable container for carrying said sample to the input chamber by movement of the container relative to the input chamber, said movable container having a discharge location in said chamber and said second outlet being upstream of said discharge location in the flow direction of said liquid sample.

13. Apparatus according to claim 11 further having suction means connected to said second outlet port for sucking washing liquid from said input chamber.

14. Apparatus according to claim 11 having a valve for controlling flow of washing liquid via said second outlet port.

15. Apparatus for analyzing particles contained in at least one liquid sample, comprising
   (i) a detector for the particles,
   (ii) a detection passage for liquid flow extending past said detector, so that said particles passing along said detection passage are detected by said detector for analysis, the detection passage being provided as part of a flow cell,
   (iii) an input location for the at least one liquid sample at an upstream end of said detection passage,
   (iv) means for causing said liquid flow along said detection passage so as to move the at least one liquid sample from said input location,
   (v) at least one liquid sample holder for holding the at least one liquid sample,
   (vi) a movable container for carrying the at least one liquid sample to the input location from said at least one sample holder, by movement of the movable container relative to the input location, wherein said movable container is a pipette, and there are a plurality of sample holders each accessible by said pipette,
   (vii) means, different from said movable container, for supplying washing liquid to said input location, and (viii) means for supplying carrying liquid to said detection passage so as to establish therein sheath flow in which the flowing carrying liquid entrains the liquid sample as a thin stream in the carrying liquid, to carry the liquid sample past the detector, said means for supplying carrying liquid including at least one carrying liquid inlet of the flow cell connected to said detection passage and a connector external to the flow cell for supply of carrying liquid, said connector being adapted to be sealingly and detachably engaged with said carrying liquid inlet.

16. Apparatus according to claim 15 wherein said plurality of sample holders are arranged on a movable carrier, for sequential presentation to said pipette.

17. Apparatus according to claim 16 wherein said pipette is adapted to sequentially carry the plurality of liquid samples to said input location from the respective sample holders.

18. Apparatus according to claim 15 wherein said connector is adapted to make a plug-type engagement with said carrying liquid inlet, and one of said connector and said input has a resilient ring seal for making sealing engagement with the other.

19. Apparatus according to claim 15 wherein the means for causing said liquid flow along said detection passage so as to move said at least one liquid sample from said input location is suction means for applying suction pressure to said detection passage to cause liquid flow.

20. Apparatus for analyzing particles contained in at least one liquid sample, comprising
   (i) a detector for the particles,
   (ii) a detection passage for liquid flow extending past said detector, so that said particles passing along said detection passage are detected by said detector for analysis,
   (iii) an input location for the at least one liquid sample at an upstream end of said detection passage, said input location having a nozzle from which the at least one liquid sample exits into a carrying liquid, said carrying liquid passing to said input location to act as washing liquid by reverse flow through the nozzle, the input location having an output passage for said washing liquid,
   (iv) means for causing said liquid flow along said detection passage so as to move the at least one liquid sample from said input location, including means for supplying said carrying liquid to said detection passage such that the carrying liquid provides sheath flow along the detection passage entraining the at least one liquid sample as a thin stream in the flowing carrying liquid,
   (v) at least one liquid sample holder for holding the at least one liquid sample,
   (vi) a movable container for carrying the at least one liquid sample to the input location from said at least one sample holder, by movement of the movable container relative to the input location, and
   (vii) means, different from said movable container, for supplying the washing liquid to said input location, said means for supplying a carrying liquid constituting said means for supplying washing liquid, whereby said carrying liquid acts as said washing liquid.

21. Apparatus for analyzing particles contained in a liquid sample, comprising
  (i) a detector for the particles,
  (ii) a detection passage for liquid flow extending past said detector, so that said particles passing along said detection passage are detected by said detector for analysis, said detection passage having an input end at which said sample enters the passage,
  (iii) an input chamber at said input end of said passage, having an inlet for delivery of said sample to said chamber, a first outlet port connecting directly to said detection passage and a second outlet port for outflow of washing liquid,
  (iv) means for causing liquid flow along said detection passage so as to move the liquid sample from said input chamber past said detector, wherein said means for causing liquid flow along said detection passage is adapted to supply a carrying liquid which creates sheath flow in said detection passage entraining the liquid sample emerging from said first outlet port as a thin stream in the carrying liquid, said carrying liquid also acting as said washing liquid by reverse flow through said first outlet port, and
  (v) means for supplying said washing liquid to said input chamber.

22. Apparatus for analyzing particles contained in at least one liquid sample, comprising
  (i) a detector for the particles,
  (ii) a detection passage for liquid flow extending past said detector, so that said particles passing along said detection passage are detected by said detector for analysis,
  (iii) an input location for the at least one liquid sample at an upstream end of said detection passage,
  (iv) means for causing said liquid flow along said detection passage so as to move the at least one liquid sample from said input location,
  (v) at least one liquid sample holder for holding the at least one liquid sample,
  (vi) a movable container for carrying the at least one liquid sample to the input location from said at least one sample holder, by movement of the movable container relative to the input location, wherein said movable container is a pipette, and there are a plurality of sample holders each accessible by said pipette,
  (vii) means, different from said movable container, for supplying washing liquid to said input location,
  (viii) a sample input to said detection passage, adapted to receive delivery of said liquid sample from the movable container, the sample inlet including a deformable mouth portion for engagement with the movable container, and
  (ix) at least one carrying liquid inlet to said detection passage for supply of carrying liquid so as to establish sheath flow in said detection passage in which the flowing carrying liquid entrains the liquid sample to a thin stream in the carrying liquid.

* * * * *